US00PP18176P3

(12) United States Plant Patent
Bak et al.

(10) Patent No.: US PP18,176 P3
(45) Date of Patent: Oct. 30, 2007

(54) ***VRIESEA* PLANT NAMED 'STYLE'**

(50) Latin Name: ***Vriesea* sp.**
Varietal Denomination: Style

(75) Inventors: Elly Bak, Rijsenhout (NL); Nico D. M. Steur, Oude Niedorp (NL)

(73) Assignee: Corn. Bak B.V., Assendelft (NL)

( * ) Notice: Subject to any disclaimer, the term of this patent is extended or adjusted under 35 U.S.C. 154(b) by 0 days.

(21) Appl. No.: 11/298,471

(22) Filed: Dec. 12, 2005

(65) Prior Publication Data

US 2007/0136917 P1 Jun. 14, 2007

(30) Foreign Application Priority Data

Mar. 16, 2005 (EM) ..... 20050488

(51) Int. Cl.
*A01H 5/00* (2006.01)

(52) U.S. Cl. ..... Plt./371

(58) Field of Classification Search ..... Plt./370
See application file for complete search history.

(56) References Cited

PUBLICATIONS

Internet website; http://www.fngla.org/tpie/newPlants.asp (3pages total).*

* cited by examiner

*Primary Examiner*—Kent Bell
*Assistant Examiner*—S. B. McCormick-Ewoldt
(74) *Attorney, Agent, or Firm*—Foley & Lardner LLP

(57) ABSTRACT

A new and distinct *Vriesea* plant named 'Style' characterized as funnel form rosette plant, measuring about 45 cm in height and 35 cm to 45 cm in diameter, and produces compound, red, bipinate spike inflorescence, measuring 20 cm to 30 cm, about 2 to 6 branches, measuring about 12 cm to 17 cm in length and 3.5 cm to 5 cm in width, and green foliage, measuring 20 cm to 30 cm in length and about 4.0 cm in width.

1 Drawing Sheet

Latin name of the genus and species of the plant claimed: *Vriesea* sp.
Variety denomination: 'Style'.

BACKGROUND OF THE INVENTION

The present invention relates to a new and distinct cultivar of *Vriesea* plant, botanically known as *Vriesea* sp., hereinafter referred to by the cultivar name 'Style'. The genus of *Vriesea* belongs to the Bromeliaceae family.

The new *Vriesea* cultivar is a product of a planned breeding program conducted by the inventors, Elly Bak and Nico D. M. Steur, in Assendelft, The Netherlands. The objective of the breeding program is to develop a new *Vriesea* variety good growing habit and attractive red inflorescence.

The new *Vriesea* cultivar 'Style' originated from a cross-made in a controlled breeding program by the Inventors in 1991 in Assendelft, The Netherlands. The female or seed parent is the *Vriesea poelmanii* cultivar designated '9120911' (unpatented). The male or pollen parent is the *Vriesea* sp. cultivar designated '86395' (unpatented). 'Style' was discovered and selected by the inventors in June of 1994, as a single flowering plant within the progeny of the stated cross in a controlled environment in Assendelft, The Netherlands.

Asexual reproduction of the new cultivar 'Style' performed by vegetative means by tissue culture was first performed in 1997, in Assendelft, The Netherlands. The first 'Style' plants propagated through the use of tissue culture flowered in 2002, in Assendelft, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'Style' which in combination distinguish this *Vriesea* as a new and distinct cultivar:

1. Funnel form rosette plant, measuring about 45 cm in total height and 35 cm to 45 cm in diameter;
2. Compound, red, bipinate spike inflorescence, measuring about 20 cm to 30 cm in height;
3. About 2 to 6 branches, measuring about 12 cm to 17 cm in length and about 3.5 cm to 5 cm in width; and
4. Green foliage, measuring about 20 cm to 30 cm in length and about 4.0 cm in width.

Plants of the parents, '9120911' (unpatented) and '86395' (unpatented), are no longer available to provide a botanical comparison with the new *Vriesea* cultivar 'Style'. *The new cultivar 'Style' differs from 9120911 with a more branched inflorescence with wider branches on a shorter stem*.

Of the many commercial cultivars known to the present inventors, the most similar in comparison to the new *Vriesea* cultivar 'Style' is the *Vriesea* cultivar designated 'Saturn' (patented, EU 15605). Plants of the new cultivar 'Style' differ from plants of 'Saturn' primarily in leaf color and a more compact growth.

BRIEF DESCRIPTION OF THE PHOTOGRAPH

The accompanying photograph illustrates the overall appearance of the new *Vriesea* cultivar 'Style' showing the colors as true as is reasonably possible with colored reproductions of this type. Colors in the photograph may differ slightly from the color values cited in the detailed botanical description which accurately describes the color of 'Style'.

The photograph shows a side view perspective of a typical potted flowering plant of 'Style' at about 17 months of age.

DETAILED BOTANICAL DESCRIPTION

'Style' has not been observed under all possible environmental conditions. The phenotype of the new cultivar may vary with variations in environment such as temperature, light intensity, day length, fertilizers and humidity without any change in the genotype of the plant.

The aforementioned photograph, together with the following observations, measurements and values describe the new *Vriesea* cultivar as grown in a greenhouse in Assendelft, The Netherlands, under conditions which closely approximate those generally used in commercial practice. Plants of 'Style' were grown in a greenhouse with day temperatures ranging from 20° C. to 28° C. and night temperatures ranging from 18° C. to 23° C. No artificial lighting or photoperiodic treatments were conducted, but plants of 'Style' are forced into flowering by adding acetylene. The following fertilizer is added when growing plants of 'Style': 1 part nitrogen, 0.6 parts phosphor, 2 parts Kalium and 0.1 parts magnesium.

Color references are made to The Royal Horticultural Society Colour Chart (R.H.S.), except where general colors of ordinary significance are used. Color values were taken under daylight conditions in a greenhouse in Assendelft, The Netherlands. The age of the plants of 'Style' described is about 17 months.

Classification:
- *Botanical.*—*Vriesea* sp.

Parentage:
- *Male parent.*—*Vriesea* sp. cultivar designated '86395' (unpatented).
- *Female parent.*—*Vriesea poelmanii* cultivar designated '9120911' (unpatented).

Propagation: Tissue culture.

Plant:
- *General appearance and form.*—Height: About 45 cm. Width: About 35 to 45 cm. Shape: Funnel form rosette.
- *Growth habit.*—Stemless.
- *Plant vigor.*—Good.
- *Flowering season.*—A fully grown plant can flower year round, starting 15–17 weeks after induction of natural light or trough treatment with acetylene.
- *Cold tolerance.*—Frost tender. Temperatures below 5° C. may damage plants.
- *Fragrance.*—None.

Foliage:
- *Quantity.*—About 25 to 35.
- *Size of mature leaf.*—Length: About 20 to 30 cm. Width: About 4.0 cm.
- *Overall shape.*—Linear, lanceolate.
- *Apex shape.*—Cuspidate and bending downward.
- *Base shape.*—Strap-like around central axis.
- *Margin.*—Entire.
- *Texture.*—Smooth and glabrous.
- *Color.*—Leaf color can vary somewhat depending on growing conditions. Upper Surface: Mature leaf: Yellow-green, RHS 147 A, with purple coloring at base, RHS 71A. Immature leaf: Green, RHS 137 A. Lower Surface: Mature leaf: Yellow-green, RHS 147 B. Immature leaf: Green, RHS 137 A.
- *Venation.*—Pattern: Parallel, unclear and not always visible.

Inflorescence:
- *Quantity and form.*—1 flower per floral bract, typical for the genus *Vriesea;* flowering is normally in progression from base to tip of scape.
- *Shape.*—Bipinate spike.
- *Size.*—About 20 cm to 30 cm in height.
- *Corolla.*—Size: Length: About 5.0 cm Width: About 0.8 cm Form: Long and narrow, petals and sepals fused at the base around the ovary. Number: About 40 to 100 depending on the size of plant.
- *Petals.*—Number: 3 per flower. Length: About 5 cm to 6 cm. Width: About 0.8 cm. Overall Shape: Ligulate. Apex Shape: Cuspidate. Base Shape: Fused. Color: Upper surface: Yellow, RHS 5 A. Lower surface: Yellowish translucent, closest to RHS 5A.
- *Sepals.*—Number: 3 per flower. Length: About 3 cm. Width: About 1 cm. Overall Shape: Ligulate. Apex Shape: Acute. Base Shape: Fused. Color: Translucent, closest to RHS 5A.
- *Branches.*—Quantity: About 2 to 6. Length: About 12 cm to 17 cm. Width: About 3.5 cm to 5 cm. Texture: Spike. Color: Red, closest to RHS 46 A.
- *Bracts.*—Quantity of bracts on main spike: About 14 to 26. Arrangement: Alternate. Size: Length: About 4.0 cm to 5.0 cm. Width: About 6.5 cm to 7.5 cm. Margin: Entire. Overall shape: Ovate. Color: Red, closest to RHS 46A.

Reproductive organs:
- *Androecium.*—Stamen: Number: 6 per flower. Length: About 5 cm. Diameter: About 0.1 cm. Color: Cream, closest to RHS 11 D. Anther. Shape: Versatile. Length: About 0.7 cm. Color: Yellow, closest to RHS 11 C. Pollen: Amount: Scarce. Color: Yellow, closest to RHS 11 C.
- *Gynoecium.*—Pistil: Number: 1 per flower. Length: About 5 cm. Stigma: Shape: 3-parted. Width: About 0.4 cm. Color: Yellow green, closest to RHS 144 C. Style: Length: About 5 cm. Color: Yellow, closest to RHS 11 C. Ovary: Shape: Conical. Length: About 0.8 cm. Diameter: About 0.3 cm. Color: Cream, about RHS 11 D.

Seeds: None produced.

Fruit: None produced.

Disease/pest resistance: No information is currently available.

Disease/pest susceptibility: No information is currently available.

I claim:

1. A new and distinct *Vriesea* plant named 'Style', substantially as illustrated and described herein.

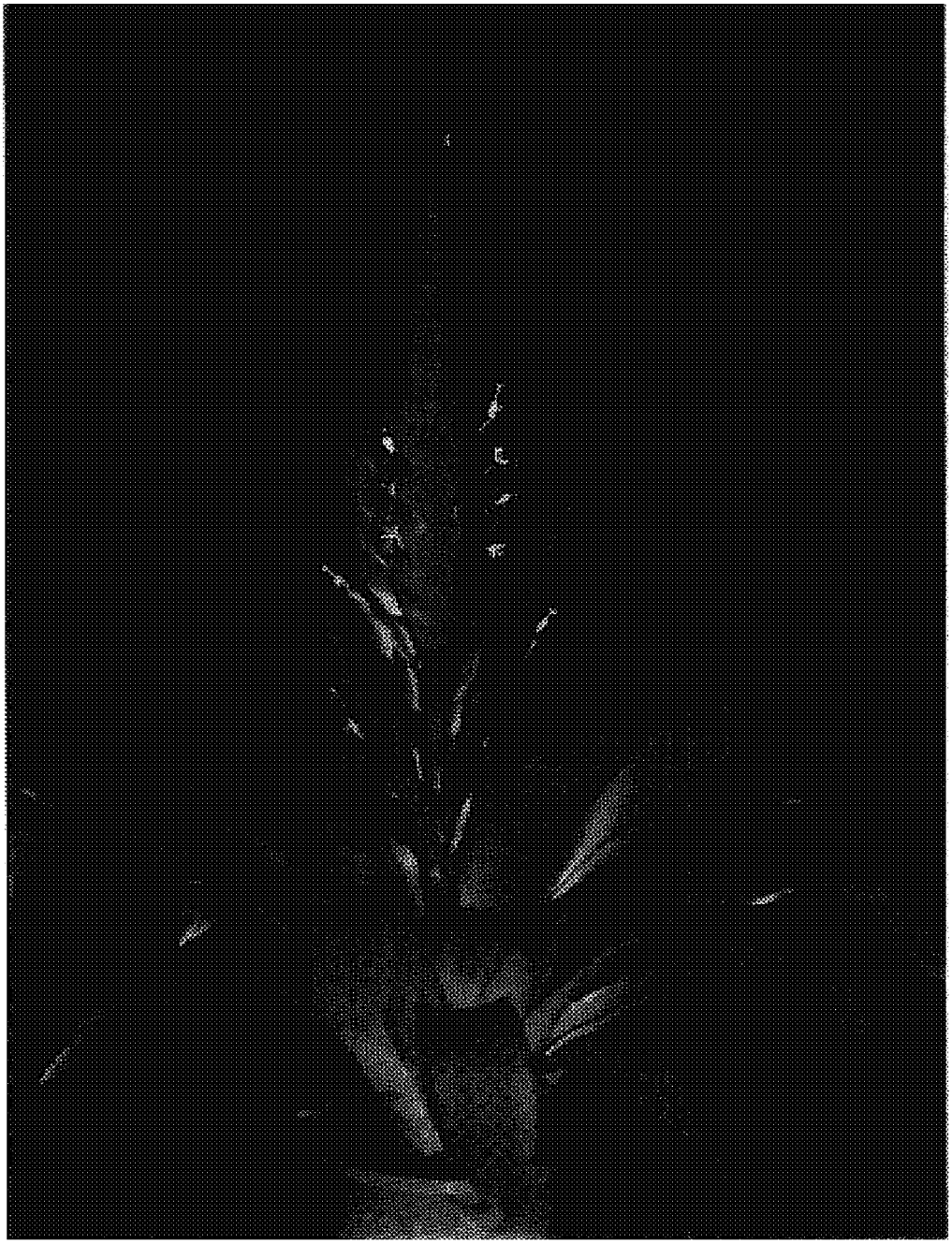

* * * * *